United States Patent [19]

Cooper et al.

[11] Patent Number: 5,444,876
[45] Date of Patent: Aug. 29, 1995

[54] CONVERTIBLE PROTECTIVE EYEWEAR

[75] Inventors: James M. Cooper, Countryside; Donald L. Rohrs, Overland Park; David D. McCormick, Prairie Village, all of Kans.

[73] Assignee: Parmelee Industries, Inc., Lenexa, Kans.

[21] Appl. No.: 189,596

[22] Filed: Jan. 31, 1994

[51] Int. Cl.$^6$ .............................................. A61F 9/02
[52] U.S. Cl. ......................................... 2/450; 2/441; 2/452
[58] Field of Search .................. 2/450, 448, 449, 452, 2/441, 443; 351/121, 116, 106

[56] References Cited

U.S. PATENT DOCUMENTS

| | | |
|---|---|---|
| D. 314,391 | 2/1991 | Nussbicki . |
| 1,845,582 | 2/1932 | Courtright ...................... 351/121 X |
| 2,379,928 | 7/1945 | Rosenheim ...................... 351/121 X |
| 2,660,092 | 11/1953 | Bloom .............................. 2/450 X |
| 2,846,684 | 8/1958 | Hill .................................... 2/441 |
| 3,233,250 | 2/1966 | Jonassen ........................... 2/443 |
| 4,017,165 | 4/1977 | Davis . |
| 4,153,347 | 5/1979 | Myer . |
| 4,348,775 | 9/1982 | Haslbeck ........................... 2/452 |
| 4,391,498 | 7/1983 | Rengstorff . |
| 4,964,714 | 10/1990 | Weymouth et al. . |
| 4,991,952 | 2/1991 | Grau . |

FOREIGN PATENT DOCUMENTS

| | | |
|---|---|---|
| 146058 | 4/1952 | Australia . |
| 0795810 | 5/1958 | United Kingdom ............. 2/443 |

Primary Examiner—Peter Nerbun

[57] ABSTRACT

Protective eyewear having a wrap-around type lens and a frame which surrounds the upper and side edges of the lens. The frame includes a slot to receive the lens, and the slot has spaced pawls within the slot. The lens includes mating detents within the face of the lens to receive the pawls and thus retain the lens to the frame. The lateral edges of the frame include upper and lower struts and a bracing bar extends vertically between the struts to define an airflow opening. Rearward of the bracing bar a paint hinge posts extend from the struts in coaxial spaced opposed relation. The temple for the eyewear includes a hinge end having a pivot hole for receiving the hinge posts. The pivot hole includes a cutout with a height corresponding to that of one of the hinge posts, and a width slightly less than that of this hinge post. The temple may thus be mounted and removed from the hinge posts by inserting a first hinge post into the hinge hole, and then snapping the cutout over the remaining hinge post. Where a goggle configuration is preferred, looped ends of an elastic band may be placed over the hinge posts. To increase airflow and/or increase eye protection, a deflector may be removably connected over the airflow opening to guide air behind the lens. The deflectors may be employed with either the temples or the elastic band.

14 Claims, 2 Drawing Sheets

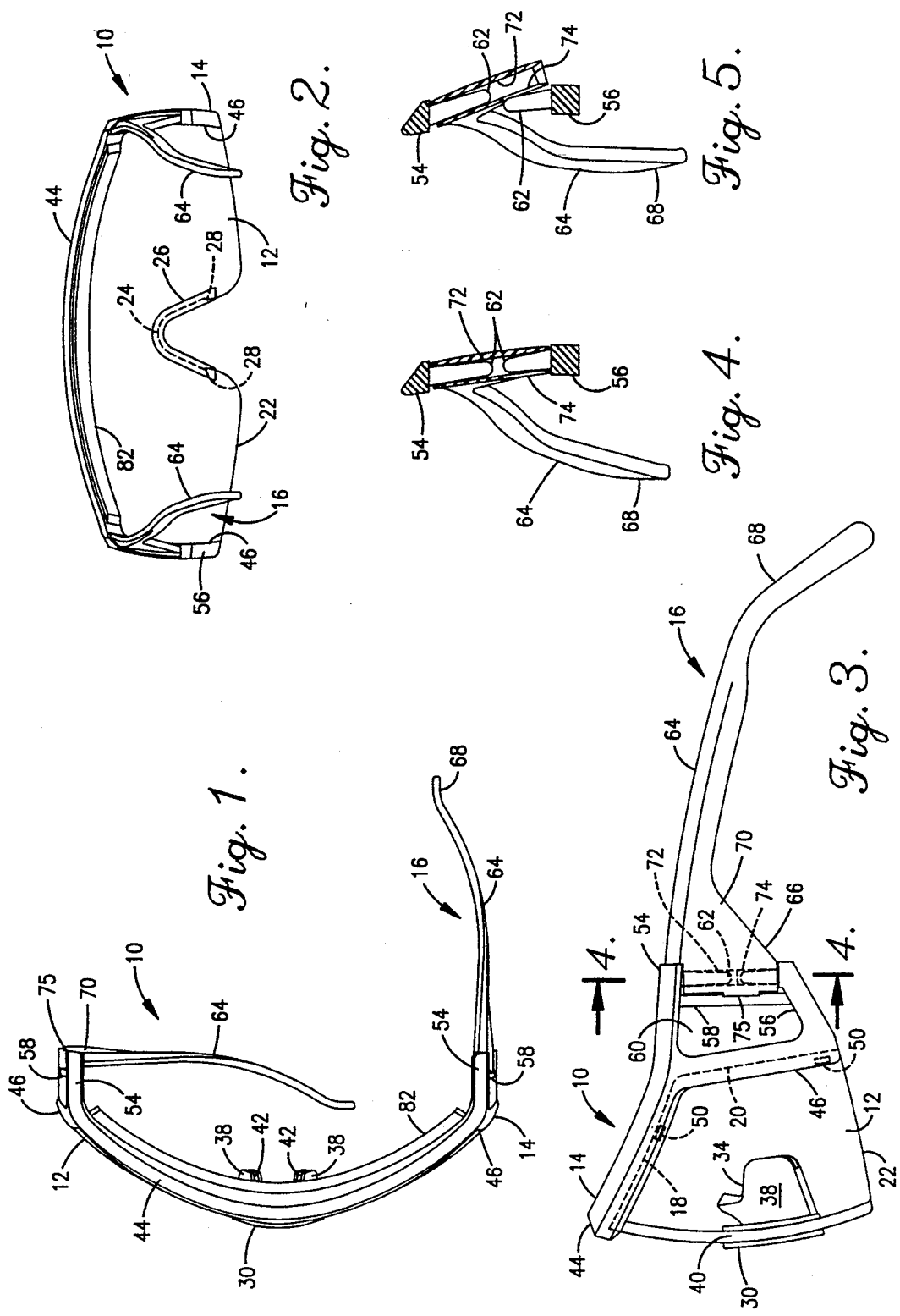

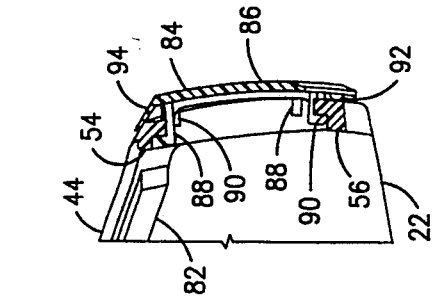
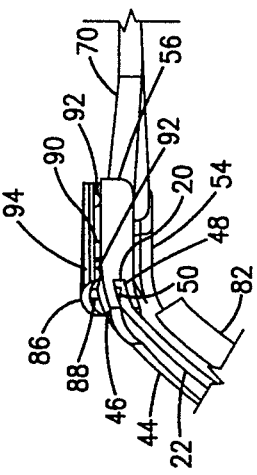
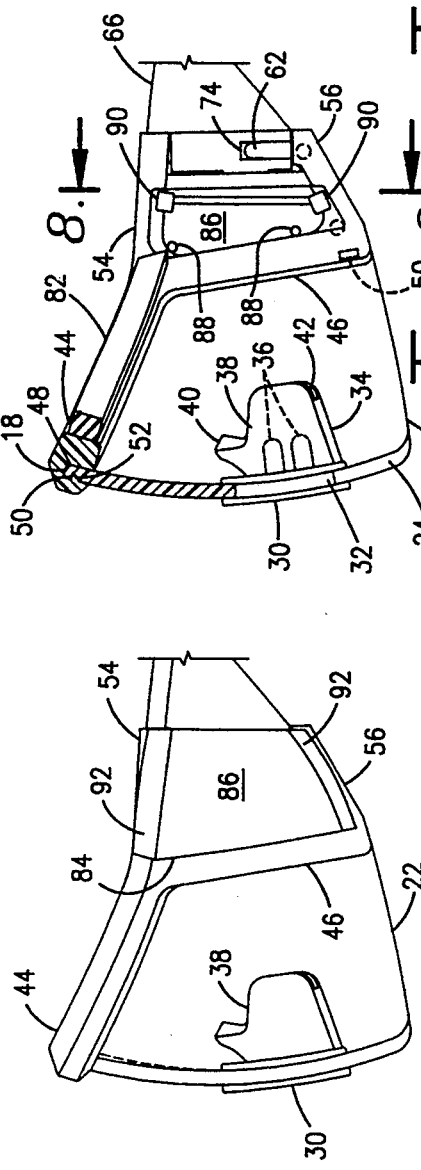
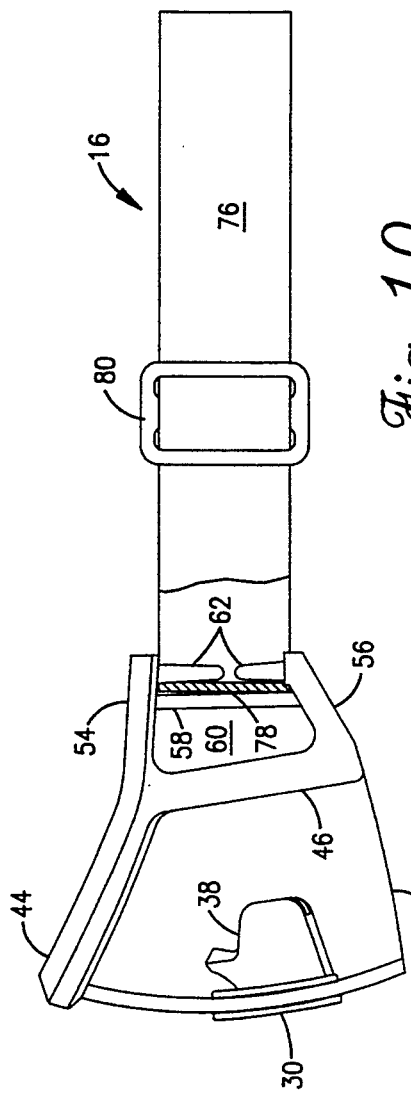

CONVERTIBLE PROTECTIVE EYEWEAR

BACKGROUND OF THE INVENTION

1. Field of the Invention

The present invention relates in general to protective eyewear. In particular, the present invention relates to improved protective eyewear which may convert from eyeglasses with temples to goggles with an elastic band.

2. Description of the Related Art

Protective eyewear for use in industrial settings and for use in sports activities typically take the form of eyeglasses and goggles. Eyeglasses include earpieces or temples extending rearward from the lenses to engage the sides of the user's head. Goggles include an elastic band connected at each end to the sides of the lenses and which will extend about the user's head. The choice between these two styles has often been a matter of personal preference. However, it has been necessary to purchase one or the other type.

In either industrial or sports settings it has also been known that protective eyewear reduces airflow about the eye region, losing much of the natural cooling such airflow provides. There have therefore been various attempts to increase airflow behind the lens to help cool the user. These attempts involved removing sections of the frame to create spaces between the user's face and the frame or lenses, which spaces allow air to flow therethrough.

Finally, in recent years it has been increasingly common to form eyeglasses which are modular, such that various components may be replaced with components having a different color or styling to create aesthetically pleasing eyewear.

SUMMARY OF THE INVENTION

An object of the present invention is to provide protective eyewear having modular components.

Another object of the present invention is to provide earpieces or temples which may be easily removed from the frame to allow replacement with like components having different colors or stylings.

Another object of the present invention is to provide such a frame with the ability to mount an elastic headband upon removal of the temples, to thus permit conversion of the eyewear from eyeglasses to goggles.

A further object of the present invention is to provide eyewear which provides good airflow behind the lens(es).

Yet another object of the present invention is to provide such eyewear which allows the selective addition of deflectors to channel air behind the lenses and further increase airflow and/or provide additional eye protection.

Another object of the present invention is to provide a lens attachment to the frame which is simple yet secure.

A further object of the present invention is to provide such a lens attachment in the form of detents or cavities extending into the face of the lens, with the frame having mating pawls or protrusions which engage with the detents to secure the lens to the frame.

These and other objects are achieved by protective eyewear having a wrap-around type lens and a frame which surrounds the upper and side edges of the lens. The frame includes a slot to receive the lens, and the slot has spaced pawls therein. The lens includes mating detents within the face of the lens to receive the pawls and thus retain the lens to the frame. The lower edge of the lens includes a nose cutout, and may be provided with a removable nosepiece. The lateral edges of the frame include upper and lower struts extending rearward. A bracing bar extends vertically between the struts and is spaced from the frame to define an airflow opening. Rearward of the bracing bar a pair of hinge posts extend from the struts in coaxial spaced opposed relation. The temple for the eyewear includes a hinge end having a pivot hole for receiving the hinge posts. The pivot hole includes a cutout with a height corresponding to that of one of the hinge posts, and a projected width slightly less than that of this hinge post. The temple may thus be mounted by inserting a first hinge post into the hinge hole, and then snapping the cutout over the remaining hinge post. Where a goggle configuration is preferred, looped ends of an elastic band may be placed over the hinge posts. To increase airflow and/or increase eye protection, a deflector may be removably connected over the airflow opening to guide air behind the lens. The deflectors may be employed with either the temples or the elastic band.

BRIEF DESCRIPTION OF THE DRAWINGS

The objects and features of the invention noted above are explained in more detail with reference to the drawings, in which like reference numerals denote like elements, and in which:

FIG. 1 is a top view of eyewear according to the present invention with temples attached;

FIG. 2 is a rear view of the eyewear of FIG. 1 with both 1.0 temples extended;

FIG. 3 is a left side view of the eyewear of FIG. 2;

FIG. 4 is a cross-sectional view along line 4—4 of FIG.

FIG. 5 is a cross-sectional view similar to FIG. 4 showing mounting and removal of the temple;

FIG. 6 is a left side view showing deflectors attached;

FIG. 7 is a cross-sectional side view showing interior attachment of the deflectors;

FIG. 8 is a cross-sectional view along line 8—8 of FIG.

FIG. 9 is a bottom view along line 9—9 of FIG. 7; and

FIG. 10 is a left side view in partial cross-section with an elastic band attached.

DETAILED DESCRIPTION OF THE INVENTION

With reference to FIGS. 1-3, eyewear according to the present invention is generally designated by reference numeral 10. The eyewear 10 generally includes a wrap-around lens 12, a frame 14, and means 16 for securing the eyewear to the user.

The lens 12 may of course take many configurations. For example, the lens may be spherical, cylindrical, torric, or have other shapes. In the preferred embodiment the lens is spherical, with one preferred range of radii being between 8.9 and 11.4 cm (3.5 and 4.5 inches). The lens preferably has a uniform transparent finish, although two areas of transparency corresponding to the positions of the eyes are all that is strictly required. The lens may be tinted or have coatings or other means for reducing light transmission, but are preferably clear.

As is best seen by comparison of FIGS. 2 and 3, the lens 12 has a laterally extending upper edge 18 which will extend across the brow of the user. The lens has lateral edges 20 extending downward from the upper edge, and a laterally extending lower edge 22 to define a roughly rectangular periphery. A nose cutout 24 (FIG. 2) having a generally triangular shape is centrally located and extends upward from lower edge 22.

The nose cutout 24 may rest directly upon the bridge of the user's nose. However, for improved comfort and to reduce slippage, it is preferred to provide a nosepiece 26 mounted upon the lens. Any standard nosepiece arrangement may be connected to the lens. It is preferred, however, that the nosepiece be removable. Such a removable nosepiece is best shown in FIGS. 1, 2 and 7.

As is shown in FIG. 2, the nose cutout 24 includes a pair of laterally extending ledges 28 which will serve to removably hold the nosepiece in position. The nosepiece 26 includes a nose section 30 having an apex configuration corresponding to that of the cutout 24. Nose section 30 includes a lens groove 32 (FIG. 7) along its outer periphery, with the lens groove sized to closely receive the edge of the lens in the nose cutout. The length of the outer periphery is such that the lower ends of the nose section rest upon the ledges 28 to thus maintain the nose section in position.

While the nose section itself could rest upon the user's nose, it is preferred that the nose section be formed of a relatively rigid plastic and mount a nose pad 34 of relatively softer plastic. To this end it is preferred that the nose section include a pair of mounting fingers 36 (FIG. 7) extending rearward from each leg of the apex of the nose section. The mounting fingers are preferably formed as a monolithic portion of the nose section.

The nose pad 34 includes a pair of rests 38 extending along the legs of the apex of the nose section and adapted to engage the user's nose on either side of the bridge. The pad 34 may also include a tie bar 40 extending across the apex to provide additional cushioning for the user's nose, and connecting the rests 38. The rests 38 are preferably formed of a resilient material for comfort. To increase the resilience of the pads, a slit 42 (FIG. 1) may extend into the rear of each pad. The rests 38 include mating cavities to receive the mounting fingers 36 extending from the nose section. The mounting fingers may secure the pad 34 to the nose section 30, or may simply locate the pad with respect to the nose section with the pad being adhesively secured.

The removable nature of the nosepiece allows replacement 1.0 due to wear. This also allows nosepieces of different configuration to be used at the user's discretion. Similarly, the nosepiece may be replace by another nosepiece having a different color or style to allow the user to customize the eyewear.

The frame 14 is preferably formed of an at least partially resilient plastic and includes a top section 44 which extends laterally along the upper edge 18 of the lens. Integrally connected to the top section 44 are lateral end sections 46 which extend downward along each lateral edge 20 of the lens to the lower edge 22 of the lens. While the frame could extend a lesser or greater extent about the periphery of the lens, this arrangement provides a secure attachment between the lens and frame, yet also allows for easy detachment.

Various arrangements are possible for attaching the lens to this frame. Permanent attachment is possible with adhesives or ultrasonic bonding. However, as noted above it is preferred to allow detachment of the lens from the frame. For such a detachable mounting it is preferred that the frame 14 include a channel 48 extending along the inner periphery of the frame and adapted to closely receive the upper and lateral edges 18 and 20 of the lens, as best seen by comparison of FIGS. 3, 7 and 9. There may then be provided various arrangements of mating protrusions and recesses between the edges of the lens and the interior of the channel of the frame.

For example, there may be provided laterally extending protrusions (not shown) formed by raised or inwardly extending bumps within the channel near the upper and lower ends of the lateral end sections 46 of the frame. These protrusions will mate with recesses (not shown) extending peripherally inwardly from the lateral edges of the lens to thus restrict movement of the lens downward with respect to the frame. This will maintain the lens in position, yet flexing the frame outward from the lower edge of the end section 46 will release the protrusions from the recesses to permit the lens to be removed.

In the preferred embodiment shown in the drawings, a side edge (in this case the outer side edge) of the channel 48 is provided with a plurality of cantilevered pawls 50 (best shown in FIGS. 7 and 9) extending toward the other sidewall of the channel. The pawls may have various locations (and may extend from both channel sidewalls), but it is preferred that the pawls be located adjacent the lower ends of the lateral end sections 46, and on the top section 46 in a central location and adjacent each lateral end (see FIGS. 3 and 7). The lens 12 will be provided with mating detents 52 extending into the face or "plane" of the lens (i.e., generally normal to the face of the lens) at positions spaced peripherally inward of, and about, the periphery and corresponding to the locations of the pawls. The pawls and detents are preferably formed with angles (FIG. 7) which cause the pawl to take the form of a barb resisting removal of the pawl from the detent.

The frame also includes upper and lower struts 54 and 56 which extend rearward from each of the lateral end sections 46. As is best shown in FIG. 3, the upper strut connects to the end section adjacent the top section 44, and is preferably styled to appear as a continuation of the top section. The lower strut 56 is connected adjacent the lower end of the end section 46, and for styling may be angled upward as shown in the drawings.

Extending vertically between each set of upper and lower struts is a bracing bar 58. The bracing bar 58 is preferably spaced from the associated lateral end section 46. As such, the struts, end section and bracing bar will define an airflow opening 60. This opening will permit air to flow behind the lens to cool the user.

A hinge post 62 is mounted upon each of the struts adjacent its free end. The hinge posts of each set of struts are cantilevered members extending substantially vertically in coaxial spaced opposed relation. As is shown in FIG. 3, the hinge posts preferably have a slight inward taper toward their free ends, which are preferably rounded.

The hinge posts, with other elements, allow the eyewear of the present invention to easily convert between use as eyeglasses-type eyewear and goggles-type eyewear. The eyeglasses-type eyewear will be described first, with reference to FIGS. 1-5 and 9.

With reference to FIGS. 1-3, the eyewear may be provided with a pair of earpieces or temples 64 in the form of elongated members pivotally mounted to the frame and adapted to pass behind the ears of the user, as is generally known. The temples will pivot between a closed and an open position shown respectively in the upper and lower halves of FIG. 1. The temples include a front pivot end 66 and a rear end 68. The rear end 68 may take various forms commonly known in the art, and will typically include a downward curvature to pass behind the user's ears.

The pivot end 66 of each temple 64 is somewhat vertically widened to approximate the vertical height of the associated struts. In the embodiment shown, this vertical widening is in the form of a solid flange 70, although other arrangements are possible. The flange 70 may be styled to form a continuation of one or both of the struts, as shown. The portions of the forward end of the flange which form such a continuation may be flattened to abut against the free end of the strut(s) when the temple is in the open position.

The flanges also include a pivot hole 70 (FIGS. 3–5) extending therethrough. The pivot holes 70 extend substantially vertically and have a diameter to permit a pivotal fit over the associated hinge posts 62. The top and bottom ends of the pivot hole are spaced a distance substantially equal to the distance from the roots of the associated hinge posts, such that when the hinge posts are received within the pivot hole there is little vertical movement of the temples with respect to the hinge posts, and thus the frame.

As shown in FIGS. 3–5, the pivot holes each include a cutout 74 extending from a first longitudinal end of the hole, which may be either the top or bottom end of the pivot hole. The cutout has a length slightly greater, and a projected width slightly less, than the associated hinge post. This will permit the associated hinge post to pass through the cutout, yet will result in the pivot hole, in the area of the cutout, having an angular extent sufficient (at least greater than 180°) to retain the hinge post and permit pivoting.

The attachment and detachment of the temple are illustrated in FIGS. 4 and 5. To mount the temple, the end of the pivot hole opposite the cutout is slid over the associated hinge post. This is possible due to the spacing between the free ends of associated hinge posts, and will require some resilient deformation of the hinge post as shown in FIG. 5. Once this hinge post is fully received within the pivot hole the cutout 74 will be adjacent the remaining hinge post. The cutout is then forced over this hinge post to achieve the posit-ion shown in FIG. 4. At this time the temple is fully attached, and will freely pivot between the open and closed position, yet is securely retained upon the frame. Detachment of the temple is achieved by reversing these steps.

As may be seen, this arrangement permits a secure pivotal attachment of the temple, yet allows easy detachment of the temple. This facilitates the conversion between eyeglasses-type eyewear and goggles-type eyewear. This also facilitates the replacement of the temples with other temples having different shapes and/or colors.

The open position of the temples is preferably a limit position, with pivoting of the temples beyond the open position being restricted. This may be accomplished by the flat end of the flange 70 abutting against the free end(s) of the strut(s). Alteratively or additionally, there may be provided a wing 75 extending forward from the pivot flange, forward of the pivot hole, on the laterally exterior face of the temple flange. As seen by comparison of FIGS. 1, 3 and 7, the wing 75 will abut against the bracing bar 58 when the temple reaches the open position, restricting further movement in the direction of opening.

The goggles-type eyewear option will now be discussed with reference to FIG. 10. As may be seen, the struts, bracing bar and hinge posts are maintained in position for this second option. Since these elements are maintained, there is no need for difficult modification of the eyewear, and these elements may be formed as a monolithic unit, as by molding.

This option employs an elastic strap 76 having two ends. Each of the ends is folded over and connected to the strap to define a loop 78. The folded over ends may be permanently secured to the strap as by adhesive or sewing, but it is preferred that at least one of the ends be connected to the strap by an appropriate adjustment buckle 80 to permit adjustment of the length of the strap to the user's head. To attach the strap, each of the loops 78 (one shown) may then be threaded through the gap between the free ends of the hinge posts 62, such that the hinge posts extend into the loop 78 as shown in FIG. 10. Detachment of the loop is performed by reversing these steps.

As may be envisioned, this is an extremely simple method of attaching the strap, yet will securely retain the strap in position. In particular, it is noted that the looped end remains looped during mounting and dismounting. The strap may be further secured by placing the bracing bar 58 close to the hinge posts to cause a close sliding fit on the strap between the bracing bar and hinge posts.

Where the eyewear is employed as goggles there is an increased tendency for the top section 44 of the frame to press against the user's brow. To improve comfort, there may be provided a cushion strip 82, for example of foam, extending across the top section 44 of the frame along its interior. This strip 82 may be permanently secured by adhesive, or removably secured by a pressure sensitive adhesive.

The above described eyewear will thus easily convert between eyeglasses and goggles. This conversion requires no tools, and only requires that the user be provided with temples and a strap. Additionally, there are no other elements removed or added for either option, eliminating the possibility of losing necessary parts. This arrangement therefore allows the user to determine which type of eyewear is preferred for a particular activity and quickly convert the eyewear to conform to these desires.

The description above is sufficient for eyewear convertible between eyeglasses and goggles. Various other options are available, however, for improving performance or appearance. As an example, there may be provided deflectors 84, shown in FIGS. 6–9. The deflectors attach to the frame over the openings 60. The deflectors may take many forms, such as a plurality of vertical or horizontal vanes, but in the preferred embodiment have a main body 86 in the general shape of a plate. The laterally interior face of each deflector includes at least one placer rod 88 cantilevered therefrom and adapted to abut against one or more edges of the opening 60.

The placer rod(s) act with at least one resilient hook 90, which extends from the interior face of the main body in a similar manner. The hook(s) 90 engage with one or more of the struts 54 or 56, frame ends section 46 or bracing bar 58. In the embodiment shown, two hooks are provided and releasibly engage with appropriate indentations on the laterally interior face of the struts.

As may be envisioned, this arrangement will allow the deflectors to be attached and removed quickly and easily.

The deflector main body has a size slightly greater than that of the opening 60, to thus cover the opening when attached. The deflector could abut against the exterior of the opening to substantially seal same against ingress of objects to thus increase eye protection. This will substantially eliminate airflow through the opening 60, however. To allow airflow, it is preferred that there be provided spacer lugs 92 on the interior face of the main body, with the lugs 92 located to abut against the laterally exterior face of the struts and/or frame end to thus space the main body from the opening. To reduce the possibility of ingress of foreign objects while still maintaining airflow, there may be provided upper and lower deflector flanges 94 along the upper and lower edges of the deflector. These flanges will taper inward toward the struts to reduce the opening between the deflector and the frame along the upper and lower edges of the deflector, while maintaining the front and rear edges of the deflector open for ventilation.

As with the nosepiece and the temples, the deflectors may be replaced quickly and easily without tools and with no other parts removed or added. The deflectors could of course be replaced with other deflectors having different styling, colors, or functions. As may also be seen, the attachment of the deflectors does not interfere with, and is not dependent upon either the temples or the elastic band. As such, the deflectors may be employed with the eyewear in either the eyeglasses or goggles configuration.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. In eyewear having at least one lens, and at least one frame section, the improvement comprising:
    said frame including a pair of hinge pins located adjacent each lateral end of said eyewear, said pins of each said pair extending towards each other generally vertically in coaxial spaced opposed relation; and
    a temple associated with each said pair of hinge pins, each said temple including a pivot end having a pivot hole receiving an associated pair of said hinge pins, each said pivot end including a cutout at a first longitudinal end of said pivot hole, said cutout having a length slightly greater than, and a projected width slightly less than, said hinge pin extending into said first longitudinal end, whereby said hinge pin extending into said first longitudinal end may pass through said cutout while the remaining hinge pin of said hinge pin pair is received within said pivot hole to allow said temple to be attached to, and removed from, said frame.

2. The improvement of claim 1, wherein said frame includes end sections mounted at the laterally exterior ends of said eyewear, and further comprising upper and lower struts extending rearward from each said end section, one said hinge post extending from each of said upper and lower struts, and further comprising a bracing bar extending between each of said upper and lower struts substantially parallel to said hinge pins, and wherein said temple includes a wing mounted on a laterally exterior face and extending forward such that said wing will be placed in abutment with said bracing bar when said temple has reached an open position.

3. The improvement of claim 2, wherein said bracing bars are spaced from said end sections such that said end section, struts and bracing bar each define an airflow opening, and further comprising a deflector removably mounted laterally exterior of each said opening.

4. The improvement of claim 3, wherein said deflector takes the general from of a plate laterally spaced from said opening.

5. In eyewear having at least one lens and at least one frame section, the improvement comprising:
    said frame including a pair of hinge pins located adjacent each lateral end of said eyewear, said pins of each said pair extending towards each other generally vertically in coaxial spaced opposed relation; and
    an elastic band having a loop at each end thereof, each said loop extending fully about an associated pair of said hinge pins as the only connection between said band and said frame, said band having a thickness such that said loops of said elastic band may pass between said pins of said associated pair to allow said elastic band to be attached to, and removed from, said eyewear.

6. The improvement of claim 5, wherein said frame includes end sections mounted at the laterally exterior ends of said eyewear, and further comprising upper and lower struts extending rearward from each said end section, one said hinge post extending from each of said upper and lower struts, and further comprising a bracing bar extending between each of said upper and lower struts substantially parallel to said hinge pins, such that said bracing bar serves to limit movement of said loop extending about said hinge pin pair.

7. The improvement of claim 6, wherein said bracing bar is spaced from said hinge pins a distance to provide a sliding fit for said elastic band loop.

8. The improvement of claim 9, wherein each said bracing bar is spaced from an associated one of said end sections such that said end section, struts and bracing bar each define an airflow opening, and further comprising a deflector removably mounted laterally exterior of each said opening.

9. The improvement of claim 8, wherein said deflector takes the general from of a plate laterally spaced from said opening.

10. In eyewear having at least one lens and at least one frame section, the improvement comprising:
    said frame including end sections mounted at the laterally exterior ends of said eyewear, and further comprising upper and lower struts extending rearward from each said end section, and further comprising a bracing bar extending between each of said upper and lower struts, each said bracing bar being spaced from an associated one of said end sections such that said end section, struts and bracing bar together define an airflow opening, and further comprising a deflector removably mounted laterally exterior of each said opening.

11. The improvement of claim 10, wherein each said deflector takes the general form of a plate laterally spaced from said opening.

12. The improvement of claim 10, wherein each said deflector includes at least one placer rod and one hook extending laterally inward for engagement with the inner periphery of said opening to thus mount said deflector.

13. The improvement of claim 12, wherein each said deflector takes the general from of a plate laterally spaced from said opening.

14. The improvement of claim 13, wherein each said deflector takes the general from of a plate laterally spaced from said opening.

* * * * *